United States Patent

Winkelmann et al.

[11] 4,046,896
[45] Sept. 6, 1977

[54] 1-METHYL-2-(PYRIDYL-OXYMETHYL)-5-NITRO-IMIDAZOLES

[75] Inventors: Erhardt Winkelmann, Kelkheim, Taunus; Wolfgang Raether, Dreieichenhain, both of Germany

[73] Assignee: Hoechst Aktiengesellschaft, Franfurt am Main, Germany

[21] Appl. No.: 686,540

[22] Filed: May 14, 1976

[30] Foreign Application Priority Data

May 17, 1975 Germany .................. 2522176

[51] Int. Cl.² ............ A61K 31/44; C07D 233/22
[52] U.S. Cl. ............... 424/263; 260/294.9; 260/296 AE

[58] Field of Search .......... 260/294.86, 294.9, 296 R, 260/296 AE, 309; 424/263

[56] References Cited

U.S. PATENT DOCUMENTS

| 3,491,105 | 1/1970 | Klink et al. | 260/296 R |
| 3,828,056 | 8/1974 | Kreider | 260/296 R |

*Primary Examiner*—Alan L. Rotman
*Attorney, Agent, or Firm*—Curtis, Morris & Safford

[57] ABSTRACT

The invention provides 1-methyl-2-(pyridyl-oxymethyl)-5-nitro-imidazoles and processes for preparing them. The compounds are useful in the therapy of diseases provoked by protozoa.

3 Claims, No Drawings

1-METHYL-2-(PYRIDYL-OXYMETHYL)-5-NITRO-IMIDAZOLES 1-(2'-Hydroxyethyl)-2-methyl-5-nitro-imidazole (Metronidazole) is used for the therapy of diseases caused by protozoa, for example trichomoniasis and amebiasis.

The present invention relates to 1-methyl-2-(pyridyl-oxymethyl)-5-nitro-imidazoles of the formula I

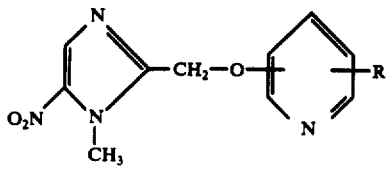

in which R represents the nitro or cyano group, and in which the pyridyl radical is bound in the 2-, 3- or 4-position to the oxygen atom.

The novel compounds are active against many species of protozoa, in particular against trichomonads and amoebas.

The invention furthermore relates to processes for preparing 1-methyl-2-(pyridyl-oxymethyl)-5-nitro-imidazoles of the formula I, which comprise a. reacting a 1-methyl-2-subst. methyl-5-nitro-imidazole of the formula II

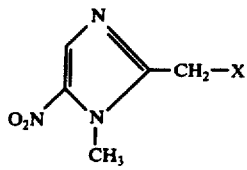

in which X represents a halogen atom such as fluorine, chlorine, bromine or iodine, or an acyloxy group such as the acetyloxy, propionyloxy, butyryloxy, benzoyloxy, nitrobenzoyloxy or toloyloxy or an arylsulfonyloxy group such as the benzoyloxy, toluenesulfonyloxy or nitrobenzene-sulfonyloxy group, with a hydroxypyridine or its alkali metal or ammonium salt of the formula III

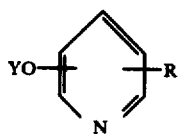

in which R represents the nitro or cyano group and Y represents hydrogen, an alkali metal or ammonium, or b. reacting 1-methyl-2-hydroxymethyl-5-nitro-imidazole of the formula IV

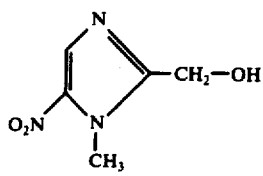

with a pyridine derivative of the formula V

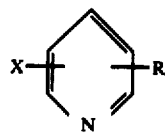

in which R and X have the meanings given for formula II or formula I.

In the process variants (a) and (b), X represents preferably halogen such as fluorine, chlorine, bromine or iodine.

As starting substances of the formula II, there may be used, for example: 1-methyl-2-chloro-, -2-bromo-, 2-iodo-methyl-5-nitro-imidazole, 1-methyl-2-acetyloxy-, -2-benzoyloxy-, -2-(4'-nitrobenzoyloxy)-, 2-toluenesulfonyloxy-methyl-5-nitro-imidazole.

As starting substances of the formula III, there may be used, for example:

2-hydroxy-3-nitro-pyridine, 2-hydroxy-5-nitro-pyridine, 2-hydroxy-3-cyano-pyridine, 2-hydroxy-5-cyano-pyridine, 3-hydroxy-2-nitro-pyridine, 3-hydroxy-6-nitropyridine, 3-hydroxy-2-cyano-pyridine, 3-hydroxy-6-cyano-pyridine, 4-hydroxy-2-nitro-pyridine, 4-hydroxy-3-nitro-pyridine, 4-hydroxy-2-cyano-pyridine, 4-hydroxy-3-cyano-pyridine.

Instead of the free hydroxy-pyridines, it is also possible to use their alkali metal salts or ammonium salts.

As starting substances of the formula V, there may be used the compounds of the formula III, in which the hydroxy group is substituted by halogen, for example fluorine, chlorine, bromine or iodine.

The variants (a) and (b) of the process of the invention are suitably carried out with equimolar quantities of the respective starting substances, advantageously in a solvent or dispersant.

As solvents for the variants (a) and (b), there may be used, for example alcohols such as methanol, ethanol, propanol, isopropanol, butanol, methoxyethano, ethoxyethanol, ketones such as acetone, methyl-ethyl ketone, methyl-butyl-ketone, amides such as dimethylformamide, diethylformamide, dimethylacetamide, furthermore N-methylpyrrolidone, tetramethyl-urea, hexamethylphosphoric acid triamide, and dimethyl-sulfoxide.

The reaction temperatures are in general between 0° and 100° C, preferably between 0° and 50° C.

The reaction times are in general some minutes and several hours, depending on the range of temperature.

If the free hydroxy-pyridines of the formula III are used, it is advisable to use also an acid-binding agent. As such an acid-binding agent, there may be used bases such as triethylamine or pyridine, as well as alkali metal and alkaline earth metal carbonates and bicarbonates, hydroxides and alkoxides, for example methoxides, ethoxides and butoxides.

Isolation of the products of the invention is carried out according to the conventional methods by distilling off the solvent used, diluting the reaction solution with water whereupon the reaction product precipitates. If necessary, a purification may follow by recrystallization from a suitable solvent or mixture of solvents.

The new compounds of the formula I are well tolerated and can be used for the therapy of diseases caused by protozoa in humans and animals, for example diseases caused by infection with trichomonas vaginalis and entameba hystolytica.

The new compounds may be administered orally or locally. Oral administration is effected in the pharmaceutically usual compositions, for example in the form of tablets or capsules, which contain, as daily dose, about 10 to 750 mg of the active substance in admixture with a usual carrier such as starch, lactose, finely divided silicic acid, talc or calcium carbonate and/or an adjuvant. For local administration, there may be used, for example gels, creams, ointments or suppositories.

The following Examples illustrate the invention:

Examples for the process variant (a)

(1.1) 1-Methyl-2-(2-nitro-pyridyl-3-oxymethyl)5-nitro-imidazole 13.8 g (0.1 mole) of powdered potassium carbonate were added to a solution of 14.0 g (0.1 mole) of 3-hydroxy-2-nitro-pyridine in 75 ml of dimethylacetamide and then a solution of 17.6 g (0.1 mole) of 1-methyl-2-chloromethyl-5 -nitro-imidazole in 75 ml of dimethylacetamide was added dropwise while stirring at 25° C. The temperature was then raised for 30 minutes to 40° - 50° C. After cooling to room temperature, the reaction mixture was poured on ice/water, the product that had precipitated was filtered off with suction and recrystallized from isopropanol with addition of charcoal.

21.5 g (77% of the theory) of 1-methyl-2-(2-nitropyridyl-3-oxymethyl)-5-nitro-imidazole were obtained in the form of cream-colored crystals, with a melting point of 170° C.

The 1-methyl-2-chloromethyl-5-nitro-imidazole used as starting compound was obtained according to DOS 1.595.929 by the reaction of 1-methyl-2-hydroxymethyl-5-nitro-imidazole (cf. DOS 1.470.102) with thionyl chloride.

Analogously to the above Example, there were obtained:

(1.2) From 1-methyl-2-chloromethyl-5-nitro-imidazole (MCNI) and 2-hydroxy-3-nitro-pyridine, 1-methyl-2-(3-nitro-pyridyl-2-oxymethyl)-5-nitro-imidazole, B.p. 269° C.

(1.3) From MCNI and 2-hydroxy-5-nitro-pyridine, 1-methyl-2-(5-nitro-pyridyl-2-oxymethyl)-5-nitro-imidazole, B.p. 251° C.

(1.4) From MCNI and 2 hydroxy-3-cyano-pyridine, 1-methyl-2-(3-cyanopyridyl-2-oxymethyl)-5-nitro-imidazole.

(1.5) From MCNI and 2-hydroxy-5-cyano-pyridine, 1-methyl-2-(5-cyano-pyridyl)-2-oxymethyl)-5-nitro-imidazole.

(1.6) From MCNI and 3-hydroxy-6-nitro-pyridine, 1-methyl-2-(6-nitropyridyl-3-oxymethyl)-5-nitro-imidazole.

(1.7) From MCNI and 3-hydroxy-2-cyano-pyridine, 1-methyl-2-(2-cyano-pyridyl-3-oxymethyl)-5-nitro-imidazole.

(1.8) From MCNI and 3 hydroxy-6-cyano-pyridine, 1-methyl-2-(cyano-pyridyl-3-oxymethyl)-5-nitro-imidazole.

(1.9) From MCNI and 4-hydroxy-2-nitro-pyridine, 1-methyl-2-(2-nitro-pyridyl-4-oxymethyl)-4-nitro-imidazole.

(2.0) From MCNI and 4-hydroxy-3-nitro-pyridine-, 1-methyl-2-(3-nitro-pyridyl-4-oxymethyl)-5-nitro-imidazole, B.p. 262° C.

(2.1) From MCNI and 4-hydroxy-2-cyano-pyridine, 1-Methyl-2-(2-cyano-pyridyl-4-oxymethyl)-5-nitro-imidazole.

(2.2) From MCNI and 4-hydroxy-3-cyano-pyridine, 1-methyl-2-(3-cyano-pyridyl-4-oxymethyl)-5-nitro-imidazole.

The compounds described in the above Example 1 could also be prepared according to method (b) by reaction of 1-methyl-2-hydroxymethyl-5-nitro-imidazole with the corresponding halogenonitropyridines or halogeno-cyanopyridines in the presence of alkali metal salts.

Examples of the process variant (b)

1-Methyl-2-(nitropyridyl-2-oxymethyl)-5-nitro-imidazole 15.7 g (0.1 mole) of 1-methyl-2-hydroxymethyl-5-nitro-imidazole were dissolved in 80 ml of dimethylformamide and heated with 14.2 g (0.1 mole) of 2-fluoro-5-nitropyridine and 13.8 g of pulverized potassium carbonate for 15 minutes to 80° C. After the usual working up (as described in Example 1), the above-specified compound was obtained with a yield of 65%. B.p. 251° C.

In the same manner, the above-listed compounds were prepared.

We claim:

1. A 1-methyl-2-(pyridyl-oxymethyl)-5-nitro-imidazole of the formula

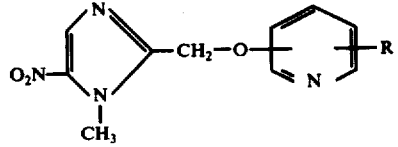

wherein R is nitro or cyano and wherein oxygen is bound to pyridyl in the 2-, 3-, or 4-position.

2. A pharmaceutical composition for the treatment of disease caused by a trichomonads or amoeba, which composition comprises a therapeutically effective amount of a compound as in claim 1 in combination with a pharmaceutical carrier.

3. A method for the treatment of disease caused by a trichomonad or amoeba in a human or animal suffering therefrom, which method comprises orally or locally administering to said human or animal a therapeutically effective amount of a compound as in claim 1.

* * * * *